US009867631B2

(12) United States Patent
Edmondson et al.

(10) Patent No.: US 9,867,631 B2
(45) Date of Patent: Jan. 16, 2018

(54) SURGICAL FORCEPS (71) Applicant: Brigham Young University, Provo, UT (US)

(72) Inventors: Bryce Edmondson, Provo, UT (US); Clayton Grames, Draper, UT (US); Landen Bowen, State College, PA (US); Eric Call, Vacaville, CA (US); Terri Bateman, American Fork, UT (US); Spencer Magleby, Provo, UT (US); Larry Howell, Orem, UT (US)

(73) Assignee: Brigham Young University, Provo, UT (US)

( * ) Notice: Subject to any disclaimer, the term of this patent is extended or adjusted under 35 U.S.C. 154(b) by 495 days.

(21) Appl. No.: 14/464,463

(22) Filed: Aug. 20, 2014

(65) Prior Publication Data
US 2015/0057702 A1 Feb. 26, 2015

Related U.S. Application Data (60) Provisional application No. 61/868,064, filed on Aug. 20, 2013.

(51) Int. Cl.
*A61B 17/29* (2006.01)
*A61B 17/28* (2006.01)
*A61B 17/00* (2006.01)

(52) U.S. Cl.
CPC .............. *A61B 17/29* (2013.01); *A61B 17/28* (2013.01); *A61B 2017/00438* (2013.01);
(Continued)

(58) Field of Classification Search
CPC ..... A61B 17/29; A61B 17/28–17/2812; A61B 17/282; A61B 2017/2926;
(Continued)

(56) References Cited

U.S. PATENT DOCUMENTS 3,392,727 A 7/1968 Hanlon
3,921,640 A * 11/1975 Freeborn ............ A61B 17/0467
30/261

(Continued)

FOREIGN PATENT DOCUMENTS

WO WO 2012/117248 A2 9/2012

OTHER PUBLICATIONS

Doria, et al., "Design of an underactuated compliant gripper for surgery using nitinol", *Journal of Medical Devices*, 3, 011007-1-011007-7; 2009.

(Continued)

*Primary Examiner* — David C Eastwood
*Assistant Examiner* — Charles Wei
(74) *Attorney, Agent, or Firm* — Sean D. Detweiler, Esq.; Morse, Barnes-Brown & Pendleton, P.C.

(57) ABSTRACT

Surgical forceps for gripping internal organs during minimally invasive surgery are provided. The surgical forceps can be a sanitizable sheet in a folded configuration that includes a first elongate region which transitions to a resilient hinge which transitions to a second elongate region, all of which are formed of the same sheet. The first elongate region can further include a first grasper end opposite the resilient hinge and the second elongate region can include a second grasper end opposite the resilient hinge. The resilient hinge can apply a spring force to the first elongate region and the second elongate region that biases the forceps in an open configuration where the first grasper end and the second grasper end are distal from each other. When an external force is applied against the resilient hinge, the first grasper end can close against the second grasper end.

18 Claims, 5 Drawing Sheets (52) U.S. Cl.
CPC ............... *A61B 2017/00526* (2013.01); *A61B 2017/2926* (2013.01); *A61B 2017/2937* (2013.01)

(58) Field of Classification Search
CPC .... A61B 2017/2931; A61B 2017/2939; A61B 2017/294; A61B 2017/2941; A61B 2017/00438
USPC ........ 606/139, 142, 143, 151–158, 205–211; 493/959
See application file for complete search history.

(56) References Cited

U.S. PATENT DOCUMENTS

| | | | | |
|---|---|---|---|---|
| 3,958,576 A * | 5/1976 | Komiya | ............... | A61B 17/083 24/456 |
| 4,192,315 A * | 3/1980 | Hilzinger | ........... | A61B 17/1227 24/565 |
| 4,360,023 A * | 11/1982 | Sugita | ................ | A61B 17/1227 606/158 |
| 4,414,721 A * | 11/1983 | Hufnagel | ............. | A61B 17/122 606/142 |
| 4,484,581 A * | 11/1984 | Martin | ................ | A61B 17/1227 606/158 |
| 4,590,937 A * | 5/1986 | Deniega | ................. | A61L 31/148 606/158 |
| 4,760,848 A * | 8/1988 | Hasson | ................. | A61B 17/062 294/115 |
| 4,765,335 A * | 8/1988 | Schmidt | ............. | A61B 17/1227 24/545 |
| 5,053,045 A * | 10/1991 | Schmidt | ............. | A61B 17/1227 606/155 |
| 5,172,700 A | 12/1992 | Bencini et al. | | |
| 2,478,376 A | 4/1994 | De Swart | | |
| 5,308,357 A * | 5/1994 | Lichtman | ........... | A61B 17/2909 606/205 |
| 5,758,420 A * | 6/1998 | Schmidt | ............. | A61B 17/1227 140/82 |
| 5,964,780 A | 10/1999 | Balazs | | |
| 6,378,351 B1 * | 4/2002 | Ouchi | .................... | B21D 35/00 606/207 |
| 6,944,914 B2 | 9/2005 | Tillim | | |
| 7,171,839 B2 * | 2/2007 | Krzyzanowski | ....... | A61B 10/06 72/336 |
| 7,727,247 B2 * | 6/2010 | Kimura | .............. | A61B 17/1222 606/142 |
| 8,585,310 B2 | 11/2013 | Mindler | | |
| 2004/0176784 A1 * | 9/2004 | Okada | ................ | A61B 17/1285 606/142 |
| 2005/0049618 A1 | 3/2005 | Masuda et al. | | |
| 2005/0054946 A1 * | 3/2005 | Krzyzanowski | ....... | A61B 10/06 600/564 |
| 2008/0140089 A1 * | 6/2008 | Kogiso | ................ | A61B 17/122 606/142 |
| 2010/0152753 A1 | 6/2010 | Menn et al. | | |
| 2010/0217294 A1 * | 8/2010 | Kimura | .............. | A61B 17/1222 606/157 |
| 2011/0046651 A1 * | 2/2011 | Cohen | ................ | A61B 17/1227 606/157 |
| 2012/0232497 A1 | 9/2012 | Sigh | | |
| 2013/0066230 A1 * | 3/2013 | Li | .......................... | B21D 11/10 600/564 |
| 2013/0072947 A1 * | 3/2013 | Terada | .................. | B21D 53/36 606/142 |

OTHER PUBLICATIONS

Frecker, et al., "Design of a multifunctional compliant instrument for minimally invasive surgery", *Journal of Biomedical Engineering Transactions of the ASME*, 127, 990-993; 2005.

Teo, et al., "Design and testing of a pressure sensing laparoscopic grasper," in *Proceedings of the 2011 Design of Medical Devices Conference*, Apr. 2011, p. 1-8.

International Search Report for International Application No. PCT/US2014/051912, dated Dec. 18, 2014.

Supplementary European Search Report from EP 14 83 7432 dated Mar. 23, 2017.

* cited by examiner

SURGICAL FORCEPS

RELATED APPLICATION(S)

This application claims priority to, and the benefit of, co-pending U.S. Provisional Application 61/868,064, filed Aug. 20, 2013, for all subject matter common to both applications. The disclosure of said provisional application is hereby incorporated by reference in its entirety.

GOVERNMENT SUPPORT

This invention was made with government support under NSF Grant No. 1240417 awarded by the National Science Foundation and Air Force Office of Scientific Research. The government has certain rights in the invention.

FIELD OF THE INVENTION

The present invention relates to surgical forceps suitable for use in minimally invasive surgery. In particular, the present invention relates to a surgical forceps that are capable of gripping internal organs during minimally invasive surgery.

BACKGROUND

Generally, minimally invasive surgery is performed by making a small incision in the body and placing a cannula through the incision to the area to be operated on. The surgical instruments are then inserted through the cannula and manipulated from outside the body. During these procedures, the surgeon is often required to expose and handle delicate tissues, organs and other structures within the body. To accomplish this, the surgeon may use forceps. Such forceps are generally inserted into the body cavity in a collapsed conformation and are guided to their intended target. Once they reach their intended target, the forceps can be expanded. The expanded configuration allows the forceps to grip tissues and organs. During the procedure, the surgeon must positively grip the tissues and organs while, at the same time, minimizing the likelihood of damage to them. This is particularly true where the tissues and organs to be gripped are thin or delicate.

However, the use of surgical forceps devices during minimally invasive surgery experiences some shortcomings. Traditional forceps are generally formed from multiple parts that move relative to one another. The parts may move by sliding, such as in a pin joint or sled guidance; by rollers, such as in ball bearings and wheels; by tipping, such as in cutting systems as used in beam and scales systems, and the like. The movement of various parts against one another invariably involves friction, which can result in wear or deformation of the forceps. The resulting wear or deformation, in turn, can prevent precise control of the forceps and impede safety. Likewise, existing forceps are often difficult to manufacture because of the many small mechanical parts used to create the forceps.

SUMMARY

There is a need for developing surgical forceps with improved manufacturability and improved safety. The present invention is directed toward further solutions to address this need, in addition to having other desirable characteristics.

In accordance to an embodiment of the present invention, surgical forceps are provided. The surgical forceps can be a sanitizable sheet in a folded configuration. The sheet can have a plurality of folds that allows the sheet to transform into the folded configuration. The sheet can further include a first elongate region which transitions to a resilient hinge which transitions to a second elongate region. The first elongate region, resilient hinge, and second elongate region can all be formed of the same sheet. The first elongate region can include a first grasper end opposite the resilient hinge, and the second elongate region can include a second grasper end opposite the resilient hinge. The resilient hinge can apply a spring force to the first elongate region and the second elongate region that biases the forceps in an open configuration where the first grasper end and the second grasper end are distal from each other. When an external force is applied against the resilient hinge of sufficient magnitude to overcome the spring force of the resilient hinge, the first grasper end can close against the second grasper end.

In accordance with aspects of the present invention, each fold of the plurality of folds can occur along a section of the sheet having a thickness dimension that is less than an average thickness dimension of the sheet at areas other than the plurality of folds. The sheet can be configured with a plurality of panels and a plurality of bridging connectors, at least one of each of the plurality of bridging connectors connecting two panels of the plurality of panels together. The plurality of bridging connectors can be selected from a group consisting of bridges, creases and channels. The plurality of folds can occur at the plurality of bridging connectors.

In accordance with yet further aspects of the present invention, the surgical forceps can be constructed of the sheet formed of a single material. The forceps can be constructed of the sheet formed of a single monolithic or composite material. The forceps can be constructed of the sheet formed of two or more layers of material adhered together. The forceps can be constructed of the sheet formed of a continuous material. The first and second elongate regions can be flat. The first and second elongate regions can be curved in one or more planes. The first and second elongate regions can be in mutual contact when the forceps are introduced into a body cavity. The first and second elongate regions can be folded flat when the forceps are introduced into a body cavity. The resilient hinge can include a diamond-like or rectangular pattern. The resilient hinge can form a 90 degree interior crease angle, a 45 degree interior crease angle, an interior crease angle of less than 90 degrees, or an interior crease angle of more than 45 degrees. The first grasper end and the second grasper end are capable of compliantly conforming in shape to an organ or structure within a body upon application of the external force against the resilient hinge.

In accordance with yet further aspects of the present invention, the surgical forceps can include a mechanism for manipulating the resilient hinge. The mechanism can cause the first grasper end and second grasper end to move relative to one another, thereby compliantly conforming in shape to an organ or structure within a body.

In accordance to an embodiment of the present invention, a method for gripping an organ or structure within a body is provided. The method can include introducing surgical forceps into a body cavity containing the organ or structure, the surgical forceps comprising a sanitizable sheet in a folded configuration having a plurality of folds, the folded configuration comprising a first elongate region which transitions to a resilient hinge which transitions to a second elongate region, the first elongate region, resilient hinge, and second elongate region all formed of the same sheet; the first elongate region having a first grasper end opposite the resilient hinge; the second elongate region having a second grasper end opposite the resilient hinge; wherein the resilient hinge applies a spring force to the first elongate region and the second elongate region that biases the forceps in an open configuration where the first grasper end and the second grasper end are distal from each other; and wherein application of an external force against the resilient hinge of sufficient magnitude to overcome the spring force of the resilient hinge causes the first grasper end to close against the second grasper end. The surgical forceps further include a mechanism for manipulating the resilient hinge. The method can further include applying the external force to cause the first grasper end and the second grasper end to compliantly conform in shape to the organ or structure and grip the organ or structure.

In accordance to an embodiment of the present invention, a kit is provided. The kit can include surgical forceps as described above. The kits can further include a port suitable for use in inserting the surgical forceps into a body cavity, wherein said port) comprises a flexible, elongate hollow tube suitable for passage of the surgical forceps therethrough.

BRIEF DESCRIPTION OF THE FIGURES

These and other characteristics of the present invention will be more fully understood by reference to the following detailed description in conjunction with the attached drawings, in which.

DETAILED DESCRIPTION

An illustrative embodiment of the present invention relates to surgical forceps for gripping internal organs during minimally invasive surgery. For example, the surgical forceps can include a sanitizable sheet in a folded configuration having a plurality of folds. In general, the folded configuration can include a first elongate region which transitions to a resilient hinge which transitions to a second elongate region. The first elongate region, resilient hinge, and second elongate region can all be formed of the same sheet. The resilient hinge can have a diamond-shaped or similar pattern, as would be appreciated by one skilled in the art. To improve manufacturability and safety, the forceps can be a single continuous structure formed from one sheet of material. The material can be a biocompatible material such as polypropylene or other similar material that is capable of gripping tissues, organs and other structures within the body without permanent or plastic deformation.

The first elongate region of the surgical forceps can further include a first grasper end opposite the resilient hinge and the second elongate region of the surgical forceps can include a second grasper end opposite the resilient hinge. The resilient hinge is capable of applying a spring force to the first elongate region and the second elongate region that biases the forceps in an open configuration where the first grasper end and the second grasper end are distal from each other. In this open configuration, the forceps can be used to grip tissues, organs and other structures within body. Application of an external force against the resilient hinge of sufficient magnitude to overcome the spring force of the resilient hinge causes the first grasper end to close against the second grasper end. In this closed configuration, the forceps can be inserted into or out of a body.

FIGS. 1A through 5B, wherein like parts are designated by like reference numerals throughout, illustrate an example embodiment or embodiments of surgical forceps for gripping internal organs during minimally invasive surgery, according to the present invention. Although the present invention will be described with reference to the example embodiment or embodiments illustrated in the figures, it should be understood that many alternative forms can embody the present invention. For example, although for purposes of clarity the example embodiments are described with reference to surgical forceps for use in minimally invasive procedures, the present invention alternatively can be implemented in accordance with forcep devices used in other procedures. Accordingly, the present invention is not limited exclusively to surgical forceps, as would be appreciated by one of skill in the art upon reading the present invention. One of skill in the art will additionally appreciate different ways to alter the parameters of the embodiment(s) disclosed, such as the size, shape, or type of elements or materials, in a manner still in keeping with the spirit and scope of the present invention.

FIGS. 1A through 5B depict perspective views of surgical forceps 10 for gripping internal organs during minimally invasive surgery, in accordance with example embodiments of the present invention. As shown in the example embodiment of FIG. 1A, the surgical forceps 10 include a sheet 12. The sheet 12 is generally sized, shaped and dimensioned to allow it be inserted into a body cavity. In some embodiments, the sheet 12 may have a width ranging between about 1 mm and about 12 mm (about 0.04 inches and about 0.5 inches). In other embodiments, the sheet 12 may have a length ranging between about 1 mm and about 12 mm (about 0.04 inches and about 0.47 inches). In other embodiments, the sheet 12 may have a thickness ranging between about 0.1 mm and about 1 mm (about 0.005 inches and about 0.047 inches). As used herein, the term "about" or "approximately" refers to a variation of 10% from the indicated values (e.g., 0.1 mm, 1 mm, 12 mm etc.), or in case of a range of values, means a 10% variation from both the lower and upper limits of such ranges. For instance, "about 1 mm" refers to a range of between 0.9 mm and 1.1 mm. The sheet 12 may be generally in the shape of an irregular octagon (as shown in FIGS. 1A through 5B), or can have a shape generally resembling a rectangular, triangular pyramid, or any other suitable shape that can be folded into the requisite forceps shape of the present invention, as would be appreciated by those of skill in the art.

Figure 1A:
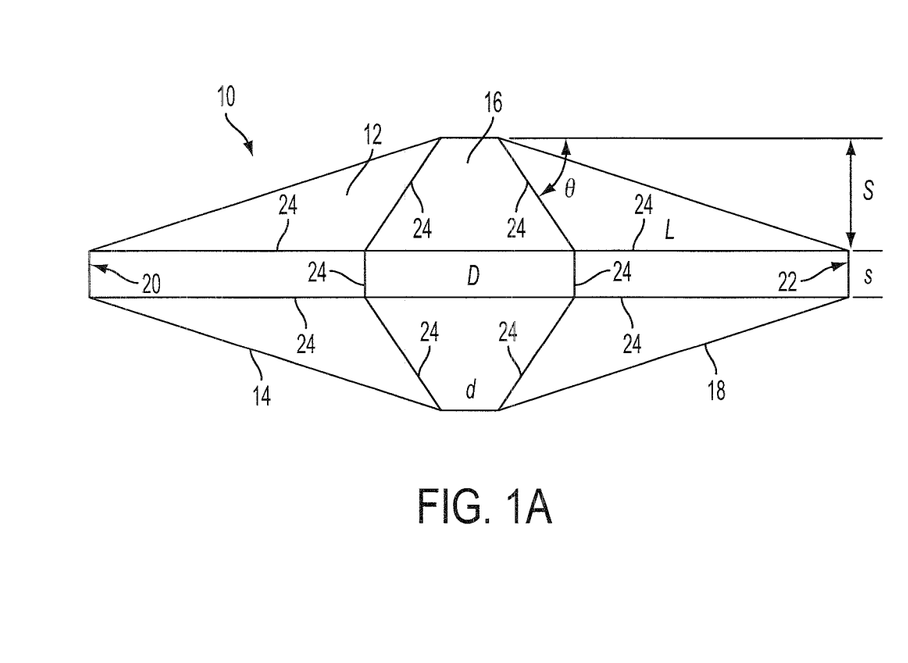
FIG. 1A is a diagrammatic illustration of a sheet with fold lines, configured to be folded to form surgical forceps, according to an example embodiment of the present invention.
Figure 1B:
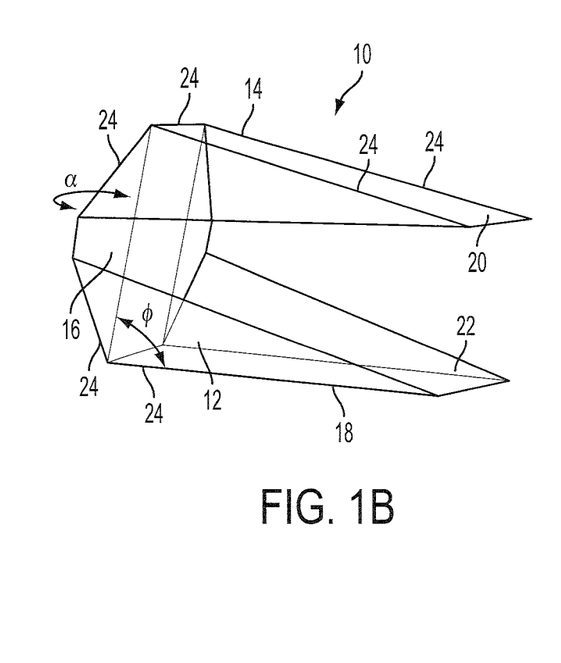
FIG. 1B is a perspective view of surgical forceps formed from the sheet, according to an example embodiment of the present invention.

In accordance with embodiments of the present invention, the sheet 12 can further include a plurality of folds 24, as shown in FIG. 1A. The plurality of folds 24 are configured to allow the sheet 12 to be folded in such a way that in a folded configuration the forceps 10 are ready for use, as shown in FIG. 1B. The transition of the sheet 12 from a flat or non-folded configuration as shown in FIG. 1A to a folded configuration as shown in FIG. 1B can occur using a process of folding. The forceps 10 of the present invention are made from relatively rigid material to allow it to grip tissues, organs and other structures without dissolving, disintegrating, flexing undesirably, or breaking apart. To make the forceps 10 foldable, the sheet 12 can include connectors or bridging connectors 26 (shown in FIG. 4) of material along each fold, which can create a smaller or thinner cross-sectional area that can more readily fold relative to the other areas of the sheet 12. This enables the forceps 10 to be substantially flat when they are inserted into a body cavity. Examples of bridging connectors 26 can include bridges, creases, channels or similar connectors as may be appreciated by one skilled in the art. In one embodiment, each fold of the plurality of folds 24 occurs along a section of the sheet 12 having a thickness dimension that is less than an average thickness dimension of the sheet 12 at areas other than the plurality of folds 24. In an embodiment, the sheet 12 can be configured with a plurality of panels and a plurality of bridging connectors 26, at least one of each the plurality of bridging connectors 26 connecting two panels of the plurality of panels together. In such a scenario, the plurality of folds 24 can occur at the plurality of bridging connectors 26.

Figure 2A:
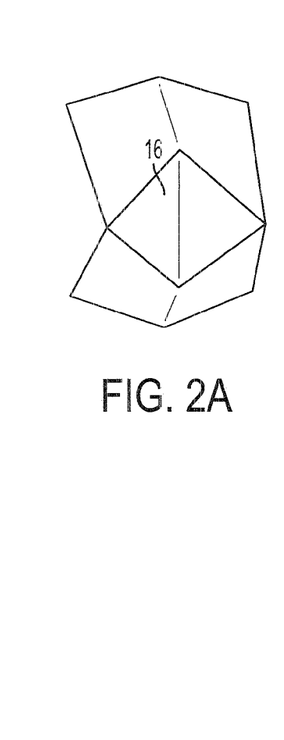
FIGS. 2A, 2B, 2C, 2D and 2E are perspective views of a resilient hinge of different configurations, according to example aspects of the present invention.
Figure 2B:
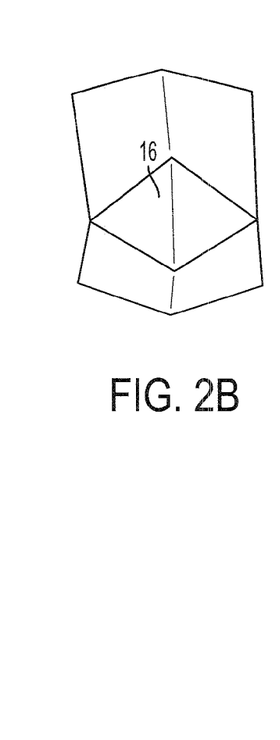
Figure 2C:
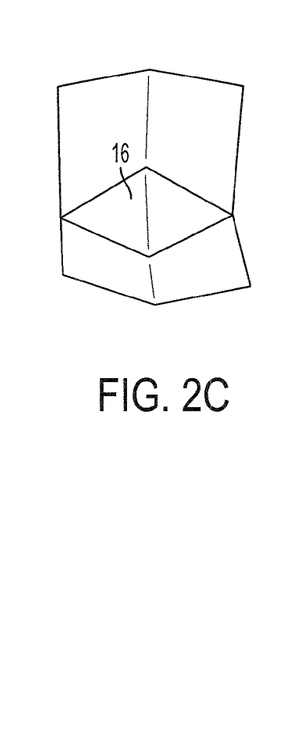
Figure 2D:
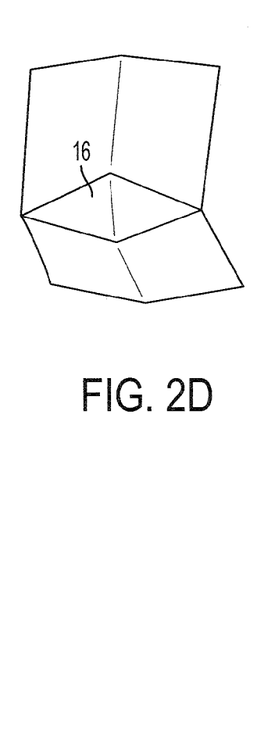
Figure 2E:
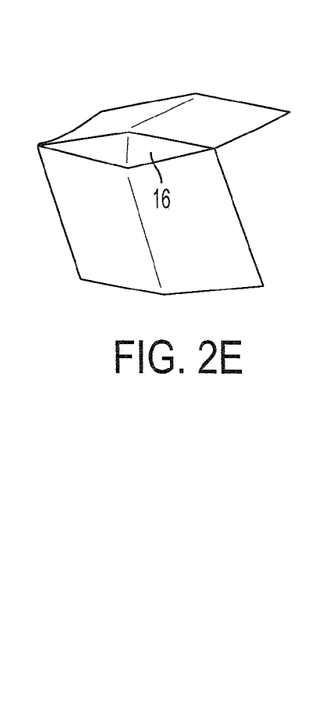

In the example embodiment shown in FIGS. 1A and 1B, the sheet 12 is formed of four sets of four symmetric folds that share a single central vertex with one common fold with adjacent sets so that bi-axis symmetry exists. This structure creates a mouth-like feature, as depicted in FIG. 1B, that can open and close in response to a force being applied to it. As shown in FIGS. 1A and 1B, this structure can be defined by the length of the side (S), length of the mouth (L), length of height (D), separation width (s), separation height (d), interior mouth angle ($\theta$, symmetric for the other interior folds), input link angle ($\alpha$), and mouth position angle ($\varphi$). The separation height and width have little to no effect on the motion of the forceps 10, but only act to increase the gripping surface and distance between the grasper ends 20, 24. As $\alpha$ approaches 180°, mechanical advantage approaches zero. The relationship between $\alpha$ and $\varphi$ changes with S, L, D, and $\theta$. As shown in FIGS. 2A through 2E, the interior crease angle, $\theta$, can be modified to alter the deflection relationship between the input and the output. FIGS. 2A through 2E show the difference between prototypes where only $\theta$ was changed. In this configuration, the interior crease angle, $\theta$, is limited to between 45°, in FIG. 2A, and 90°, in FIG. 2E. FIGS. 2B, 2C and 2D, which show prototypes where the interior crease angle is more than 45° but less than 90°. As $\theta$ approaches 45°, $\varphi$ converges to 90° making the closed jaw separation equal D. When $\theta$ approaches 90°, the input angle goes to 180°, thereby eliminating the unique forcep geometry. As would be appreciated by one skilled in the art, the crease angle may be less than 45° or greater than 90°. In the example embodiment shown in FIG. 4, the interior crease angle, $\theta$, is 70°. In addition to the parameters defined in FIGS. 1A and 1B, the flexure-based design of FIG. 4 introduces parameters for flexure length, l, and flexure width, b. Flexure length l is defined as orthogonal to the crease and width, b, is parallel to the crease. This design also assumes that the flexure thickness is equivalent to the material thickness. In an embodiment, when the forceps 10 are made with multi-layers, flexure thickness also becomes and unique parameter. In another embodiment, the stiffness of the design is proportional to the flexure width. In yet another embodiment, the torsional resistance is related to the flexure length and width.

In the example embodiments of FIGS. 1A through 5B, the forceps 10 are constructed of the sheet 12 formed of a continuous material. In such embodiments, the forceps 10 are formed from a single piece of material. For example, the forceps 10 can be formed by injection molding, laser cutting, stamping or other planar manufacturing techniques, as may be appreciated by one skilled in the art. In some embodiments, the forceps 10 may be constructed of the sheet 12 formed of a single monolithic or composite material. In other embodiments, the forceps 10 can be constructed of the sheet 12 formed of multiple pieces of materials. In yet some other embodiments, the forceps 10 can be constructed of a sheet 12 formed of two or more layers of material adhered together. In these embodiments, the layers may be adhered to one another with screws, clips, glue or other adhesives, pins, staples, tacks, welding, sintering, or the like.

Furthermore, the sheet 12 is generally formed from a material that is sufficiently flexible to allow it to grip tissues, organs and other structures within the body without permanent or plastic deformation, and also sufficiently rigid to allow it to maintain its structure in such implementations. Additionally, the sheet 12 is generally formed from a material that is sufficiently compliant to allow it to form a cup-shape around the tissues, organs and other structures within the body that it is meant to retain and/or move. The phrase "compliantly conform" as utilized herein is intended to mean that the sheet 12 can be folded into forceps 10 that are capable of forming a cup-shape when in contact with tissues, organs and other structures within the body. In some embodiments, the sheet 12 has a high elastic strain (i.e., ratio of yield strength to Young's modulus). In other embodiments, the sheet 12 has a high modulus of rigidity (i.e., yield strength squared over two (2) times the Young's modulus). In one embodiment, the material is qualified by 1000*Sy/E(yield strength to modulus ratio)>=10. In other embodiments, the material can be qualified by 1000*Sy/E(yield strength to modulus ratio)<=10. In some embodiments, the sheet 12 can be made from a material that is sanitizable to allow the forceps 10 to be reused. Alternatively, in other embodiments, the sheet 12 can be made from a single-use and/or disposable material. The sheet 12 can further be formed from a material that is biocompatible. Examples of materials suitable for use with the present invention include, but are not limited to, certain metals and plastics such as polypropylene, titanium, metallic glass, PEEK, steel, carbon fiber, shape memory alloy, shape memory polymers, Delrin®, Kevlar®, and other composite materials. Other materials are also suitable for use with the present invention, as would be appreciated by one skilled in the art.

In addition to the sheet 12, the surgical forceps 10 of FIGS. 1A through 5B also include two or more elongate regions. In the example embodiment of FIGS. 1A and 1B, the forceps 10 include a first elongate region 14 and a second elongate region 18. The elongate regions 14, 18 are generally sized, shaped and dimensioned to allow them be inserted into a body cavity. In the example embodiment of FIG. 1A, each of the elongate regions 14, 18 is substantially flat (e.g., non-curved). In the example embodiment of FIG. 1B, each of the elongate regions 14, 18 is curved in one or more planes. This transition from being flat to being curved can occur when the forceps 10 are folded and are ready for use. In the example embodiments of FIGS. 1A through 5B, each of the elongate regions 14, 18 are substantially the same width. In alternate embodiments, the elongate regions 14, 18 may have different widths. In some embodiments, the sheet 12 may have a width ranging between about 1 mm and about 12 mm (about 0.04 inches and about 0.5 inches). In the example embodiments of FIGS. 1A through 5B, each of the elongate regions 14, 18 are substantially the same length. In alternate embodiments, the elongate regions 14, 18 may have different lengths. In one embodiment, the elongate regions 14, 18 have a length ranging between about 1 mm and about 12 mm (about 0.04 inches and about 0.5 inches). In the example embodiments of FIGS. 1A through 5B, each of the elongate regions 14, 18 are substantially the same thickness. In alternate embodiments, the elongate regions 14, 18 may have different thicknesses. In one embodiment, each of the elongate regions 14, 18 may have a thickness ranging between about 0.1 mm and about 1 mm (about 0.005 inches and about 0.047 inches). The elongate regions 14, 18 may be generally triangular in shape (as shown in FIGS. 1A through 5B), or can have a shape generally resembling a cylinder, rectangle, or any other suitable shape, as would be appreciated by those of skill in the art. The elongate regions 14, 18 can be tapered at one or both ends.

In addition, each of the elongate regions 14, 18 can include a grasper end which is capable of gripping tissues, organs and other structures within the body. In the example embodiment of FIGS. 1A and 1B, the first elongate region 14 includes a first grasper end 20 opposite the resilient hinge 16, and the second elongate region 18 includes a second grasper end 22 opposite the resilient hinge 16. In some embodiments, the grasper ends 20, 22 may be smooth (as depicted in FIGS. 1A through 5B). In other embodiments, the grasper ends 20, 22 may include teeth to help it grip tissues, organs and other structures. The teeth can be continuous with the grasper ends 20, 22 or can be removably coupled to the grasper ends 20, 22. In these embodiments, the teeth may be adhered to the grasper ends 20, 22 with screws, clips, glue or other adhesives, pins, staples, tacks, welding, sintering, or the like.

Furthermore, the elongate regions 14, 18 are generally formed from a material that is sufficiently flexible to allow it to grip tissues, organs and other structures within the body without permanent or plastic deformation, and also sufficiently rigid to allow it to maintain its structure. Additionally, the elongate regions 14, 18 are generally formed from a material that is sufficiently compliant to allow it to form a cup-shape around the tissues, organs and other structures within the body that it is meant to retain and/or move. In the example embodiments of FIGS. 1A through 5B, each of the elongate regions 14, 18 have substantially the same degree of flexibility and/or compliance. In alternate embodiments, the elongate regions 14, 18 may have different degrees of flexibility and/or compliance. In some embodiments, the elongate regions 14, 18 are formed from a material that has a high elastic strain (i.e., ratio of yield strength to Young's modulus). In other embodiments, the elongate regions 14, 18 are formed from a material that has a high modulus of rigidity (i.e., yield strength squared over two (2) times the Young's modulus). In one embodiment, the material is qualified by 1000*Sy/E(yield strength to modulus ratio)>=10. In other embodiments, the material can be qualified by 1000*Sy/E(yield strength to modulus ratio)<=10. The elongate regions 14, 18 are further formed from a material that is biocompatible. Examples of materials suitable for use with the present invention include, but are not limited to, certain metals and plastics such as polypropylene, titanium, metallic glass, PEEK, steel, carbon fiber, shape memory alloy, shape memory polymers, Delrin®, Kevlar®, and other composite materials. Other biocompatible materials are also suitable for use with the present invention, as would be appreciated by one skilled in the art.

In addition to the sheet 12 and the elongate regions 14, 18, the surgical forceps 10 of FIGS. 1A through 5B can further include a resilient hinge 16 that acts to connect the first elongate region 14 to the second elongate region 18, or the second elongate region 18 to the first elongate region 14. As such, the resilient hinge 16 acts as a transition between the elongate regions 14, 18. In general, the resilient hinge 16 can have various shapes and patterns, as may be appreciated by one skilled in the art. In the example embodiment shown in FIGS. 1A and 1B and FIGS. 2A through 2E, the resilient hinge 16 can have a diamond-like pattern. In the example embodiment shown in FIG. 4, the resilient hinge 16 can have a rectangular-like pattern. Alternatively, the resilient hinge 16 can have a shape generally resembling a cylinder, triangular pyramid, rectangle or any other suitable shape, as would be appreciated by those of skill in the art.

In the example embodiments of FIGS. 1A through 5B, the elongate regions 14, 18 and the resilient hinge 16 are continuous. In such embodiments, the elongate regions 14, 18 and the resilient hinge 16 are formed from one piece of material, as depicted. For example, the elongate regions 14, 18 and the resilient hinge 16 can be formed by injection molding, laser cutting, stamping or other planar manufacturing techniques, as may be appreciated by one skilled in the art. In other embodiments, the elongate regions 14, 18 and the resilient hinge 16 may be formed from multiple pieces of materials. In these embodiments, the elongate regions 14, 18 and the resilient hinge 16 may be formed from multiple layers of materials and/or multiple components. In yet some other embodiments, the elongate regions 14, 18 may be removably coupled with the resilient hinge 16. Iii these embodiments, a fastening mechanism (e.g., screws, clips, etc.) may be used to affix the elongate regions 14, 18 to the resilient hinge 16. Alternatively, the elongate regions 14, 18 can slide in and out of the fastening mechanism. Additionally and/or alternatively, the elongate regions 14, 18 can be affixed to the resilient hinge 16 by glue or other adhesives, staples, tacks, welding, sintering, or the like.

The resilient hinge 16, furthermore, can be formed from a material that is sufficiently flexible to allow it to transition from a flat or unfolded configuration to a folded configuration without permanent or plastic deformation, and also sufficiently rigid to allow it to maintain its structure. In some embodiments, the resilient hinge 16 is formed from a material that has a high elastic strain (i.e., ratio of yield strength to Young's modulus). In other embodiments, the resilient hinge 16 is formed from a material that has a high modulus of rigidity (i.e., yield strength squared over two (2) times the Young's modulus). In one embodiment, the material is qualified by 1000*Sy/E(yield strength to modulus ratio)>=10. In other embodiments, the material can be qualified by 1000*Sy/E(yield strength to modulus ratio)<=10. In an embodiment, the resilient hinge 16 is further formed from a material that is biocompatible. Examples of materials suitable for use with the present invention include, but are not limited to, certain metals and plastics such as polypropylene, titanium, metallic glass, PEEK, steel, carbon fiber, shape memory alloy, shape memory polymers, Delrin®, Kevlar®, and other composite materials. Other biocompatible materials are also suitable for use with the present invention, as would be appreciated by one skilled in the art.

In the example embodiments of FIGS. 1A through 5B, the resilient hinge 16 is continuous with the elongate regions 14, 18. In such embodiments, the resilient hinge 16 and the elongate regions 14, 18 are formed from one piece of material. For example, the resilient hinge 16 and the elongate regions 14, 18 can be formed by injection molding, laser cutting, stamping or other planar manufacturing techniques, as may be appreciated by one skilled in the art. In other embodiments, the resilient hinge 16 and the elongate regions 14, 18 can be formed from multiple pieces of materials. In these embodiments, the resilient hinge 16 and the elongate regions 14, 18 may be formed from multiple layers of materials and/or multiple components. In yet some other embodiments, the resilient hinge 16 may be removably coupled to the elongate regions 14, 18. In these embodiments, a fastening mechanism (e.g., screws, clips, etc.) may be used to affix the resilient hinge 16 to the elongate regions 14, 18. Alternatively, the resilient hinge 16 can be affixed to the elongate regions 14, 18 by glue or other adhesives, pins, staples, tacks, welding, sintering, or the like.

Figure 3A:
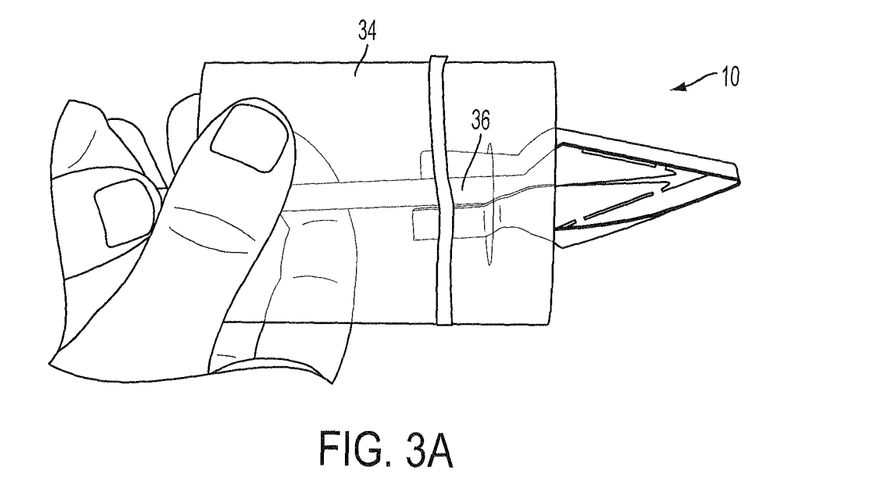
FIG. 3A and FIG. 3B are side views of progressive stages of surgical forceps being actuated in and out of a tube.
Figure 3B:
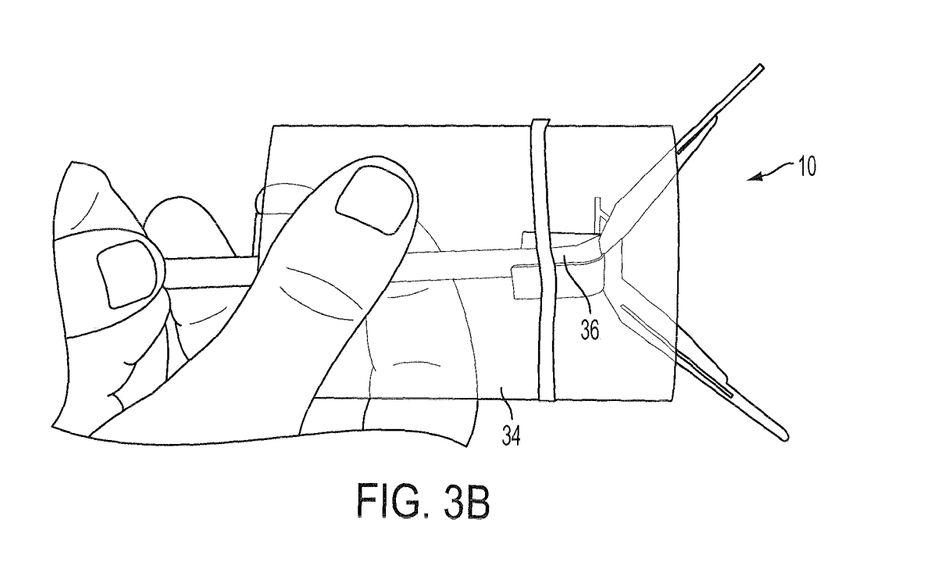
Figure 4:
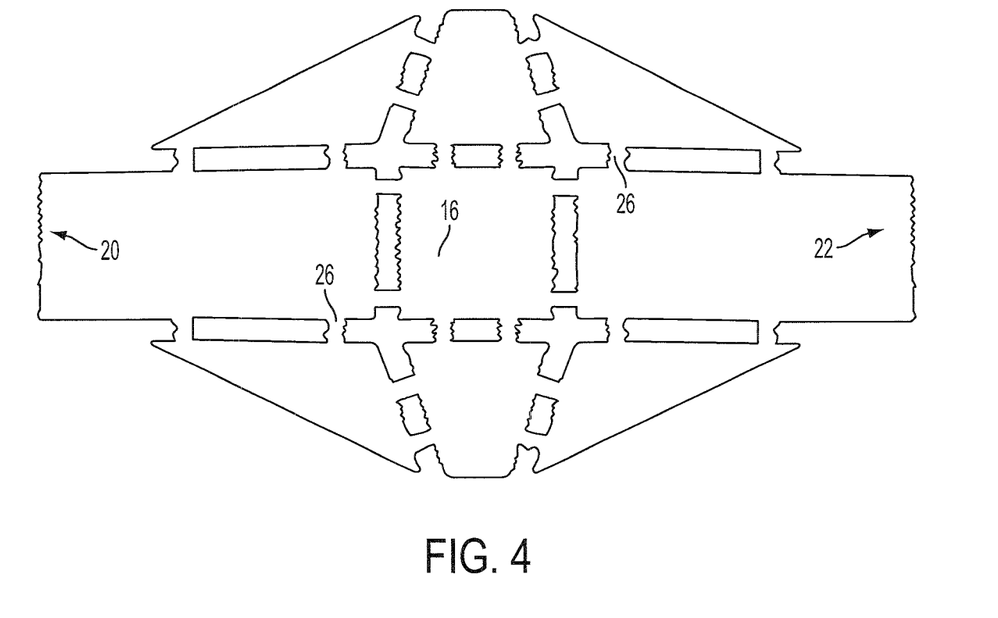
FIG. 4 is a diagrammatic illustration of surgical forceps in sheet form prior to folding, according to an example embodiment of the present invention.
Figure 5A:
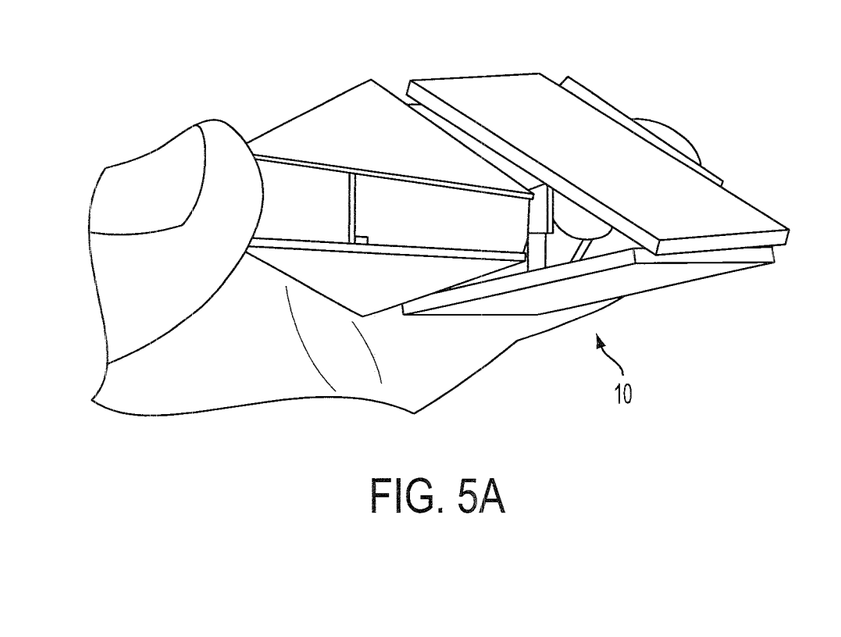
FIGS. 5A and 5B are perspective views of surgical forceps in a closed position and in an open position, respectively.
Figure 5B:
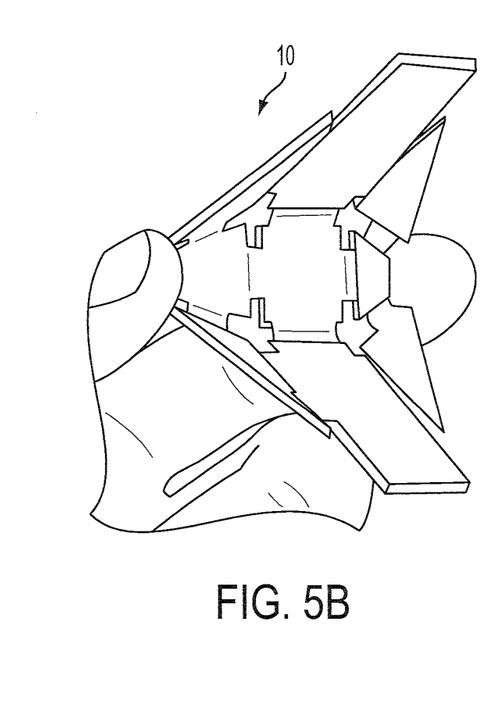

To grip tissues, organs and other structures within the body during minimally invasive surgery, the surgical forceps 10 have multiple configurations as shown in FIGS. 3A and 3B and FIGS. 5A and 5B. In one embodiment, the surgical forceps 10 have a closed configuration as shown in FIGS. 3A and 5A, an open configuration as shown in FIGS. 3B and 5B, and a partially open configuration that is in between the closed configurations of FIGS. 3A and 5A and the open configurations of FIGS. 3B and 5B. In other embodiments, the forceps 10 can have a partially opened configuration that is between the closed configuration of FIGS. 3A and 5B and the open configuration of FIGS. 3B and 5B.

In the closed configuration, the grasper ends 20, 22 are in mutual or near mutual contact with one another. When the forceps 10 are in a closed configuration (i.e., when the elongate regions 14, 18 are in mutual or near mutual contact with one another), spring force energy may be stored in the resilient hinge 16, which can help return the forceps 10 to an open configuration. In the closed configuration, application of an external force against the resilient hinge 16 is of sufficient magnitude to overcome the spring force of the resilient hinge 16 to cause the first grasper end 20 to close against the second grasper end 22 or the second grasper end 22 to close against the first grasper end 20. Alternatively, no spring force energy may be stored in the resilient hinge 16. In such circumstances, a separate device can be used to open and close the forceps 10. In this closed configuration, the forceps 10 may be introduced into a body cavity though a tube 34, as shown in FIG. 3B. Once the forceps 10 are at the location of interest within the body, the forceps 10 may be opened, The size of the organ or structure to be gripped will determine how far the forceps 10 need to be opened. In the open configuration, the first grasper end 20 and the second grasper end 22 are distal from each other. It should be noted that the term "distal" as used herein refers the grasper ends 20, 22 being separated from one another. A partially-opened configuration may be beneficial if a small-sized organ is being gripped. If a larger-sized organ is being retracted, the forceps 10 may be opened to a fully expanded configuration as shown in FIG. 3B.

The surgical forceps 10 of the present invention may be uncoated or may include a coating. The coating may be any suitable coating, including as a non-limited example, a biodegradable or bioabsorbable coating capable of carrying and delivering a therapeutic agent, and/or providing an increased degree of lubricity, as desired. Such a coating can be applied to the forceps 10 with sufficient thickness to serve as a physical protective layer) between surrounding tissue and the surface of the forceps 10. The coating can also help prevent contamination of the inner portions of the forceps 10.

The forceps 10 may further be coupled to an actuation mechanism 36 for manipulating the resilient hinge 16, as depicted in FIGS. 3A and 3B. The actuation mechanism 36 allows the operator to control the degree of opening of the elongate regions 14, 18 with a high degree of precision. The actuation mechanism can cause the elongate regions 14, 18 to move relative to each another, thereby allowing the grasper ends 20, 22 to compliantly conform in shape to the tissues, organs or other structures with the body. In one embodiment, the actuation mechanism for manipulating the elongate regions 14, 18 can be a scissor-like unit. Of course, it should be appreciated that other actuation mechanisms may also fall within the scope of the present invention as long as they are capable of opening and closing the forceps 10.

The forceps 10 may further be coupled to an anchor for anchoring and/or securing the forceps 10 to the tissues, organs or other structures within a body. The anchor can prevent the accidental removal of the forceps 10, or the tissues, organs or other structures it is holding, from the body. The anchor may also prevent movement of the forceps 10, or the tissues, organs or other structures it is holding, within the body. Examples of anchors that are capable of being used to anchor and/or secure the forceps 10 to the tissues, organs or other structures include, but are not limited to, hooks, pins, clasps, cables and other similar devices.

In operation, the forceps 10 can be used in minimally invasive surgery to grip internal tissues, organs and other structures in the body, as would be appreciated by one of skill in the art upon reading the present specification. First, the surgical forceps 10 are introduced into a body cavity through a tube or trocar in the closed configuration and are advanced to the site containing the tissues, organs and other structures. Once at the site of interest, the user can manipulate the resilient hinge 16 using an actuation mechanism 36 to cause the forceps 10 to open. For instance, by operating the actuating mechanism, the resilient hinge 16 applies a spring force to the first elongate region 14 and the second elongate region 18 that biases the forceps 10 in an open configuration. The user can then operate the actuation mechanism 36 in such a way to allow the grasper ends 20, 22 to grip the tissues, organs or other structures. By operating the actuation mechanism 36, an external force is applied to cause the first grasper end 20 and the second grasper end 22 to compliantly conform in shape to the tissues, organs and other structures within the body. When the desired tissues, organs or structures are gripped, the forceps 10 may be secured in place by an anchor.

Once the procedure is completed, the forceps 10 can be detached and/or removed by first unlocking the anchor and then manipulating the actuation mechanism 36 in such a way that the grasper ends 20, 22 release the tissues, organs or other structures and then the forceps 10 transitions to a closed configuration. This occurs when, by operating the actuation mechanism, an external force is applied against the resilient hinge 16 of sufficient magnitude to overcome the spring force of the resilient hinge 16 causing the first grasper end 20 to close against the second grasper end 22. Once in the closed configuration, the forceps 10 may be pulled through the tube or trocar and removed from the body.

The surgical forceps of the present invention may be distributed as a kit. The kit may include a surgical forceps according to any of the embodiments discussed herein and a port suitable for use in inserting the surgical forceps into a body cavity. The port can be formed from a flexible material to allow it to navigate through the body and around various tissues, organs or other structures within the body. In addition, the port can be hollow to allow passage of the surgical forceps therethrough.

Notably, the surgical forceps 10 of the present invention offer superior manufacturability in that they are capable of being manufactured from one single piece of material, for example by machining a solid block of material into the desired surgical forceps 10 shape, or as a single piece of material, such as by injection molding, 3D printing, laser cutting, stamping or other planar manufacturing techniques, rather than from multiple pieces. Moreover, manufacturing the forceps 10 in this manner allows the forceps 10 to be produced at a lower cost, which can allow for cost effective disposability and time-savings from eliminating required cleaning. By being manufactured from a single piece of material, the forceps 10 provide the added safety benefit of the forceps 10 remaining intact during a surgical procedure, thereby reducing the likelihood that pieces or sections of the forceps 10 will fall off during surgery. If the forceps 10 are reusable, manufacturing the forceps 10 from a single piece of material rather than from multiple components will improve sterilization of the forceps 10, thus reducing the likelihood that the forceps 10 may be contaminated during use. In addition to reductions in the manufacturing costs of the surgical forceps 10, there are added reductions in shipping costs when shipping the surgical forceps 10 while flat.

In addition, in accordance with embodiments of the present invention, the forceps 10 may be altered to integrate into existing actuation methods utilizing a pull/push method or similar. Furthermore, by altering the geometric configurations of the surgical forceps 10, the forceps 10 can be optimized to specific force limitations at the output beyond an input threshold that could be useful in applications that lack force feedback. Upon reading the present specification, one of skill in the art will appreciate yet further benefits not described herein.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A surgical forceps, comprising:
   a sanitizable sheet in a folded configuration having a plurality of folds, the folded configuration comprising:
   a first elongate region which transitions to a resilient hinge which transitions to a second elongate region, wherein the first elongate region, the resilient hinge, and the second elongate region are all formed of a same sheet;
   the first elongate region having a first grasper end opposite the resilient hinge;
   the second elongate region having a second grasper end opposite the resilient hinge;
   wherein the resilient hinge applies a spring force to the first elongate region and the second elongate region that biases the forceps in an open configuration where the first grasper end and the second grasper end are spaced from each other;
   wherein application of an external force against the resilient hinge of sufficient magnitude to overcome the spring force of the resilient hinge causes the first grasper end to close against the second grasper end in mutual contact; and
   wherein the sheet is configured with a plurality of panels each defined by spaces between each of the plurality of panels and a plurality of bridging connectors, and wherein each of the plurality of bridging connectors traverses the spaces and connects opposing ends of two adjacent panels of the plurality of panels together at the plurality of folds.

2. The surgical forceps of claim 1, wherein each fold of the plurality of folds occurs along a section of the sheet having a thickness dimension that is less than an average thickness dimension of the sheet at areas other than the plurality of folds.

3. The surgical forceps according to claim 1, wherein the plurality of bridging connectors are selected from a group consisting of bridges and creases.

4. The surgical forceps of claim 1, wherein the plurality of folds occur at the plurality of bridging connectors.

5. The surgical forceps of claim 1, wherein the forceps are constructed of the sheet formed of a single material.

6. The surgical forceps of claim 1, wherein the forceps are constructed of the sheet formed of a single monolithic or composite material.

7. The surgical forceps of claim 1, wherein the forceps are constructed of the sheet formed of two or more layers of material adhered together.

8. The surgical forceps of claim 1, wherein the forceps are constructed of the sheet formed of a continuous material.

9. The surgical forceps according to claim 1, wherein the first and second elongate regions are flat.

10. The surgical forceps according to claim 1, wherein the first and second elongate regions are in mutual contact when the forceps are introduced into a body cavity.

11. The surgical forceps according to claim 1, wherein the first and second elongate regions are folded flat when the forceps are introduced into a body cavity.

12. The surgical forceps according to claim 1, wherein the resilient hinge comprises a diamond-like or rectangular pattern.

13. The surgical forceps according to claim 1, wherein the resilient hinge forms a 90 degree interior crease angle, a 45 degree interior crease angle, an interior crease angle of less than 90 degrees, or an interior crease angle of more than 45 degrees.

14. The surgical forceps according to claim 1, wherein the first grasper end and the second grasper end are capable of compliantly conforming in shape to an organ or structure within a body upon application of the external force against the resilient hinge.

15. The surgical forceps according to claim 1, further comprising a mechanism for manipulating the resilient hinge.

16. The surgical forceps according to claim 15, wherein the mechanism for manipulating the resilient hinge causes the first grasper end and second grasper end to move relative to one another, thereby compliantly conforming in shape to an organ or structure within a body.

17. A kit comprising:
surgical forceps according to claim 1; and
a port suitable for use in inserting the surgical forceps into a body cavity, wherein said port comprises a flexible, elongate hollow tube suitable for passage of the surgical forceps therethrough.

18. A method for gripping an organ or structure within a body comprising the steps of:
a) introducing surgical forceps into a body cavity containing the organ or structure, comprising:
 (i) a sanitizable sheet in a folded configuration having a plurality of folds, the folded configuration comprising:
 a first elongate region which transitions to a resilient hinge which transitions to a second elongate region, wherein the first elongate region, the resilient hinge, and the second elongate region are all formed of a same sheet;
 the first elongate region having a first grasper end opposite the resilient hinge;
 the second elongate region having a second grasper end opposite the resilient hinge;
 wherein the resilient hinge applies a spring force to the first elongate region and the second elongate region that biases the forceps in an open configuration where the first grasper end and the second grasper end are spaced from each other; and
 wherein application of an external force against the resilient hinge of sufficient magnitude to overcome the spring force of the resilient hinge causes the first grasper end to close against the second grasper end in mutual contact; and
 (ii) a mechanism for manipulating the resilient hinge;
b) applying the external force to cause the first grasper end and the second grasper end to compliantly conform in shape to the organ or structure and grip the organ or structure;
wherein the sheet is configured with a plurality of panels each defined by spaces between each of the plurality of panels and a plurality of bridging connectors, and wherein each of the plurality of bridging connectors traverses the spaces and connects opposing ends of two adjacent panels of the plurality of panels together at the plurality of folds.

\* \* \* \* \*